United States Patent [19]

Keegan

[11] Patent Number: 5,001,170
[45] Date of Patent: Mar. 19, 1991

[54] DENTURE STABILIZER

[75] Inventor: James J. Keegan, Bloomfield, N.J.

[73] Assignee: Warner-Lambert Company, Morris Plains, N.J.

[21] Appl. No.: 444,658

[22] Filed: Dec. 1, 1989

[51] Int. Cl.$^5$ .......................... A61K 6/00; C08L 1/26; A61C 13/225
[52] U.S. Cl. .................................... 523/120; 524/43; 433/180
[58] Field of Search .......................... 523/120; 524/43

[56] References Cited

U.S. PATENT DOCUMENTS

| | | | |
|---|---|---|---|
| 2,978,812 | 4/1961 | Rosenthal et al. | 32/2 |
| 2,985,609 | 5/1961 | Plitt | 260/29.6 |
| 3,736,274 | 5/1973 | Schoenholz | 523/120 |
| 3,868,339 | 2/1975 | Keegan et al. | 523/120 |
| 4,280,936 | 7/1981 | Dhabhar et al. | 260/13 |
| 4,373,036 | 2/1983 | Chang et al. | 523/120 |
| 4,758,630 | 7/1988 | Shaw et al. | 525/207 |

*Primary Examiner*—Thurman Page
*Assistant Examiner*—G. S. Kishore
*Attorney, Agent, or Firm*—Charles A. Gaglia, Jr.

[57] ABSTRACT

A denture adhesive base composition comprises a substantially anhydrous mixture of methyl vinyl ether-maleic acid copolymer, polyvinyl pyrrolidone and ethylene oxide polymer. A denture adhesive composition including this base composition is also provided, the denture adhesive composition optionally including hydroxypropylcellulose. A method for formulating the novel denture adhesive base compositions and denture adhesive compositions of the invention is also disclosed.

30 Claims, No Drawings

DENTURE STABILIZER

BACKGROUND OF THE INVENTION

1. Field of the Invention

This invention relates to denture adhesives or stabilizers, and particularly to an improved anhydrous denture adhesive composition.

2. Description of the Prior Art

Traditionally, adherent powders used to secure dentures within the mouth were prepared from such materials as finely powdered natural gums, i.e. karaya, acacia or tragacanth gum. These materials have the particular property of swelling to many times their original volume upon the addition of water to form a gelatinous or mucilaginous mass. Denture adhesive powders may be a combination of one or more natural gums, generally flavored with pleasant tasting volatile oils. Many other additives may also be included, such as antiseptics, stabilizers, bactericides, special deodorants, plasticizing agents, fillers, coloring agents, and the like.

Cream forms of the denture adherent, prepared from finely ground particles of the natural gums dispersed in a cream base, are also available and may be used instead of the powder compositions. In any event, when wet with water, the natural gum in either the cream or powder formulation, expands to become a viscous gel which acts as a cushion and an adherent between the denture plate and the gum tissue.

While these relatively simple formulations are effective in securing dentures within the oral cavity for a short period of time, generally more than one application of adhesive per day is necessary. This is, at best, inconvenient and therefore, most undesirable.

In recent years, there have been numerous improvements in the above-described simple denture adhesive formulations. For example, in U.S. Pat. No. 2,978,812, a substantially anhydrous denture fixative is disclosed which includes an ethylene oxide polymer having a molecular weight between 500,000 and 5,000,000, in an amount preferably comprising at least 50% of the active fixative materials.

U.S. Pat. No. 2,985,609 discloses a water-soluble pressure-sensitive adhesive composition which consists of polyethylene amine in combination with either polyvinyl alcohol or polyvinyl pyrrolidone.

U.S. Pat. No. 3,736,274 discloses a denture adhesive containing three essential ingredients: a maleic anhydride and/or acid copolymer (with a lower alkyl vinyl ether), a polymeric N-vinyl lactam, and sodium carboxymethylcellulose, preferably incorporated into a diluent such as petrolatum and/or mineral oil.

U.S. Pat. No. 4,280,936 discloses a denture adhesive comprising sodium carboxymethylcellulose and poly(ethylene oxide) homopolymer in a mineral oil base.

U.S Pat. No. 4,373,036 discloses a denture fixative composition which includes hydroxypropylcellulose, in combination with partially neutralized polyacrylic acid, partially neutralized lower alkyl vinyl ether-maleic acid or anhydride copolymer and/or polyethylene oxide.

While all of the above denture adhesives provide some improvement over simple formulations containing only finely powdered natural gums, it is generally recognized that no one product has yet been developed which can accommodate, over a long period of time, the many variations in temperatures, pH and mechanical agitation which are quite normal in the oral cavity.

It has now been found that the denture adhesive of this invention will provide superior adherent properties over prolonged periods of time and under unusually varied conditions, without the disadvantages characteristic of previously known products.

SUMMARY OF THE INVENTION

The novel denture stabilizers formed according to the present invention are generally prepared by mixing a denture adhesive base composition with additional materials to produce denture adhesive compositions which, whether formulated in powder or paste form, exhibit excellent properties as denture stabilizers.

Applicant has unexpectedly discovered a denture adhesive base composition comprising a substantially anhydrous mixture of methyl vinyl ethermaleic acid copolymer, polyvinyl pyrrolidone and ethylene oxide polymer.

In one preferred embodiment of the invention, it has been unexpectedly discovered to form a denture adhesive composition which comprises a substantially anhydrous mixture of from about 25 to about 50 percent by weight, based on the total weight of the denture adhesive composition, of a denture adhesive base composition containing methyl vinyl ethermaleic acid copolymer, polyvinyl pyrrolidone and ethylene oxide polymer.

In another preferred embodiment, it has been unexpectedly discovered to form a denture adhesive composition comprising a substantially anhydrous mixture of:

(a) from about 25 to about 50 percent by weight, based on the total weight of the denture adhesive composition, of a denture adhesive base composition containing methyl vinyl ethermaleic acid copolymer, polyvinyl pyrrolidone and ethylene oxide polymer;

(b) from about 8 to about 20 percent by weight, based on the total weight of the denture adhesive composition, of hydroxypropylcellulose; and (c) from about 30 to about 67 percent by weight, based on the total weight of the denture adhesive composition, of additional materials selected from the group consisting of waxes, oils, preservatives, flavoring agents, colorants, sweetening agents, viscosity modifiers and mixtures thereof.

In an especially preferred embodiment, it has been unexpectedly discovered to form a denture adhesive composition comprising a substantially anhydrous mixture of:

(a) from about 5 to about 20 percent by weight, based on the total weight of the denture adhesive composition, of methyl vinyl ethermaleic acid copolymer;

(b) from about 5 to about 20 percent by weight, based on the total weight of the denture adhesive composition, of polyvinyl pyrrolidone;

(c) from about 5 to about 20 percent by weight, based on the total weight of the denture adhesive composition, of ethylene oxide polymer;

(d) from about 8 to about 20 percent by weight, based on the total weight of the denture adhesive composition, of hydroxypropylcellulose; and (e) additional materials in an amount sufficient to yield a denture adhesive composition having a total weight equal to 100 percent by weight of the total denture adhesive composition.

The invention also involves a method for preparing these novel denture stabilizers.

In one preferred embodiment, a method for preparing a denture adhesive base composition comprises:

(a) preparing a substantially anhydrous mixture of methyl vinyl ethermaleic acid copolymer, polyvinyl pyrrolidone and ethylene oxide polymer;

(b) forming a denture adhesive base composition including said mixture; and (c) recovering said denture adhesive base composition.

DESCRIPTION OF THE INVENTION

Applicant has unexpectedly discovered a novel denture adhesive base composition comprising a substantially anhydrous mixture of methyl vinyl ethermaleic acid copolymer, polyvinyl pyrrolidone and ethylene oxide polymer.

Denture adhesive compositions formed with the above-described denture adhesive base composition yield a product which provides surprising good performance as a denture stabilizer. Specifically, denture adhesives of the present invention require fewer applications per day, exhibit increased holding power (firmness) and duration of holding, and provide greater consumer confidence of product function.

The invention comprises a unique combination of three essential components, namely methyl vinyl ethermaleic acid copolymer, polyvinyl pyrrolidone and ethylene oxide polymer. In the absence of any of these components from the formulations of this invention, compositions may be prepared which do not exhibit the enhanced effect achieved from this combination.

The methyl vinyl ethermaleic acid copolymer utilized in the present invention is an anionic adhesive material which is known to those skilled in the art. A suitable methyl vinyl ethermaleic acid copolymer is commercially available from General Aniline and Film Corporation under the trademark Gantrez S-97.

Polyvinyl pyrrolidone, also named providone or PVP, is a known binding and suspending agent which is commercially available. Polyvinyl pyrrolidone, when reacted solely with methyl vinyl ethermaleic acid copolymer, forms a water insoluble complex polymer which is unusable as a denture adhesive. When the third essential component of the invention is added, the inventive denture adhesive base composition is formed.

The third essential component of the present adhesive base formulations comprises ethylene oxide polymer. Ethylene oxide polymer is a water-soluble non-ionic white powder having an average molecular weight of about 100,000 to about 5,000,000. The preferred ethylene oxide polymer utilized in the present invention is commercially available from Union Carbide Corporation under the trademark Polyox WSR 301.

When these three components are intermixed, a denture adhesive base composition is formed which exhibits superior characteristics as a denture stabilizer when incorporated into a denture adhesive composition.

The denture adhesive base composition may comprise from about 20 to about 40 percent by weight methyl vinyl ethermaleic acid copolymer, from about 20 to about 40 percent by weight polyvinyl pyrrolidone, and from about 20 to about 40 percent by weight ethylene oxide polymer, based on the total weight of the denture adhesive base composition.

Preferably, the denture adhesive base composition comprises from about 30 to about 35 percent by weight methyl vinyl ethermaleic acid copolymer, from about 30 to about 35 percent by weight polyvinyl pyrrolidone, and from about 30 to about 35 percent by weight ethylene oxide polymer, based on the total weight of the denture adhesive base composition.

The denture adhesive base compositions are useful to prepare denture adhesive compositions. According to the invention, a denture adhesive composition is provided which comprises a substantially anhydrous mixture of from about 25 to about 50 percent by weight, based on the total weight of the denture adhesive composition wherein the denture adhesive base composition contains three essential components, (a) methyl vinyl ethermaleic acid copolymer, (b) polyvinyl pyrrolidone and (c) ethylene oxide polymer. In addition to the presence of the three essential ingredients used to prepare the adhesive base composition, the inventive formulation also contemplates use of a fourth component to aid in enhancing the adhesive nature of the base composition. The optional fourth component is hydroxypropylcellulose. The hydroxypropylcellulose when present is employed in amounts up to about 20 percent by weight, based upon the total weight of the denture adhesive composition, and preferably in amounts up to about 15 percent, and most preferably in amounts of about 8 to about 20 percent by weight.

The hydroxypropylcellulose utilized in the present invention generally comprises a water-soluble, non-ionic cellulose ether having an average molecular weight of about 50,000 to about 1,500,000. A suitable hydroxypropylcellulose for use in the present invention is commercially available under the trademark Klucel HXF (Hercules).

In addition to the foregoing materials, the denture adhesive composition may be formulated with additional components well known in the denture adhesive art. Such additional materials utilized in the invention may comprise waxes, oils, preservatives, flavoring agents, colorants, sweetening agents, viscosity modifiers and so forth.

The waxes useful in the invention comprise both natural and synthetic waxes and include without limitation animal waxes such as beeswax, lanolin and shellac wax, vegetable waxes such as carnauba, candelilla and bayberry wax, mineral wax such as petroleum waxes including paraffin, and microcrystalline.

The oils useful in the invention include without limitation mineral oil, vegetable oil such as corn, soybean, cottonseed, castor, palm and coconut oils and animal oil such as fish oil, and oleic acid.

Flavoring agents well known to the denture adhesive art may be added to the compositions of the instant invention. These flavoring agents may be chosen from synthetic flavor oils and/or oils derived from plants, leaves, flowers, fruits and so forth, and combinations thereof. Representative flavor oils include: spearmint oil, cinnamon oil, oil of wintergreen (methylsalicylate) and peppermint oils. Also useful are artificial, natural or synthetic fruit flavors such as citrus oil including lemon, orange, grape, lime and grapefruit, and fruit essences including apple, strawberry, cherry, pineapple and so forth. The flavoring agent may be a liquid, spray dried, encapsulated, sorbed on a carrier and mixtures thereof. A preferred flavoring agent is peppermint oil, commercially available from Rose Mitcham. The amount of flavoring agent utilized may vary depending on such factors as flavor type, adhesive formulation and strength desired. In general, amounts of about 0.01% to about 5.0% by weight of the total denture adhesive composition are usable, with amounts of about 0.05% to 0.15% being preferred.

Preservatives which may be used in the denture adhesive formulations of the invention include those known antimicrobial agents conventionally employed in the art, such as benzoic acid and sodium benzoate; the parabens; sorbic acid and sorbates; propionic acid and propionates; acetic acid and acetates; nitrates and nitrites; sulfur dioxide and sulfites; antibiotics; diethyl pyrocarbonate; epoxides; hydrogen peroxide; and phosphates. The parabens include the methyl, ethyl, propyl, and butyl esters of parahydroxybenzoic acid. Methyl paraben and propyl paraben are the preferred preservatives of the invention, preferably utilized in amounts of about 0.03% to about 0.6% by weight of the total denture adhesive composition.

The denture adhesive compositions may also include the use of sweeteners well known in the art.

The sweetening agent may be selected from a wide range of materials including water-soluble agents, water-soluble artificial sweeteners, and dipeptide based sweeteners, including mixtures thereof. Without being limited to particular sweeteners, representative illustrations encompass:

A. Water-soluble sweetening agents such as monosaccharides, disaccharides and polysaccharides such as xylose, ribose, glucose, mannose, galactose, fructose, dextrose, sucrose, sugar, maltose, partially hydrolyzed starch, or corn syrup solids and sugar alcohols such as sorbitol, xylitol, mannitol, maltitol, hydrogenated starch hydrolysate and mixtures thereof.

B. Water-soluble artificial sweeteners such as the soluble saccharin salts, i.e., sodium or calcium saccharin salts, cyclamate salts, acesulfam-K, sucralose and the like, and the free acid form of saccharin.

C. Dipeptide based sweeteners such as L-aspartyl-L-phenylalanine methyl ester and materials described in U.S. Pat. No. 3,491,131, L-D-aspartyl-N-(2,2,4,4-tetramethyl-3-thietanyl-D-alaninamide hydrate) and the like.

In general, the amount of sweetener will vary with the desired amount of sweetener selected for a particular denture adhesive formulation. This amount may be about 0.001% to about 5% by weight of the final denture adhesive composition when using an easily extractable sweetener.

The colorants useful in the present invention include the pigments such as titanium dioxide, and may also include dyes suitable for food, drug and cosmetic applications. These colorants are known as F.D. & C. dyes. The materials acceptable for the foregoing spectrum of use are preferably water-soluble. Illustrative examples include indigo dye, known as F.D. & C. Blue No. 2, which is the disodium salt of 5,5'-indigotindi-sulfonic acid. Similarly, the dye known as F.D. & C. Green No. 1, comprises a triphenylmethane dye and is the monosodium salt of the 4-[4-Nethyl-p-sulfobenzylamino) diphenylmethylene]-[1-(N-ethyl-N-P-sulfobenzyl)-2, 5-cyclohexadienimini]. A preferred colorant is F.D. & C. Red No. 3. A full recitation of F.D. & C. and D. & C. colorants and their corresponding chemical structures may be found in the Kirk-Othmer Encyclopedia of Chemical Technology, 3rd Edition, Volume 6, at pages 561–595.

The viscosity modifiers useful herein include polyethylene and its derivatives, quaternary ammonium compounds and similar agents, starches, gums, casein gelatin and semisynthetic cellulose derivatives such as carboxymethylcellulose.

These viscosity modifiers may be further defined as they relate to each of the two blocks of the final denture adhesive composition: (a) the vehicle and (b) the gum block.

When a mineral oil vehicle is employed, polyethylene is used as a gelling agent to provide a "synthetic petrolatum" vehicle, and thus is used to adjust the extrusion (application) properties of the finished composition. Polyisobutylene may also be used in conjunction with polyethylene to further enhance the viscosity properties of the vehicle. Alternatively, a stock petrolatum, with or without mineral oil, may be employed depending upon the specific handling qualities which are desired in the final product.

The remaining viscosity modifiers useful in the present invention (quaternary ammonium compounds, sodium carboxymethylcellulose, etc.) belong to the gum block of the denture adhesive. These agents have an impact on the extrusion qualities of the adhesive, but are functionally dormant until they are activated by saliva in the mouth.

In another aspect of the invention, a denture adhesive composition is provided which comprises a substantially anhydrous mixture of:

(a) from about 25 to about 50 percent by weight, based on the total weight of the denture adhesive composition, of a denture adhesive base composition containing methyl vinyl ethermaleic acid copolymer, polyvinyl pyrrolidone and ethylene oxide polymer;

(b) from about 8 to about 20 percent by weight, based on the total weight of the denture adhesive composition, of hydroxypropylcellulose; and (c) from about 30 to about 67 percent by weight, based on the total weight of the denture adhesive composition, of additional materials selected from the group consisting of waxes, oils, preservatives, flavoring agents, colorants, sweetening agents, viscosity modifiers and mixtures thereof.

In an especially preferred aspect of the invention, a denture adhesive composition is formed which comprises a substantially anhydrous mixture of:

(a) from about 5 to about 20 percent by weight, based on the total weight of the denture adhesive composition, of methyl vinyl ethermaleic acid copolymer;

(b) from about 5 to about 20 percent by weight, based on the total weight of the denture adhesive composition, of polyvinyl pyrrolidone;

(c) from about 5 to about 20 percent by weight, based on the total weight of the denture adhesive composition, of ethylene oxide polymer;

(d) from about 8 to about 20 percent by weight, based on the total weight of the denture adhesive composition, of hydroxypropylcellulose; and (e) additional materials in an amount sufficient to yield a denture adhesive composition having a total weight equal to 100 percent by weight of the total denture adhesive composition.

The denture adhesive compositions may be in the form of a paste or powder mixture. The means for preparing such formulations is well known in the denture adhesive art.

In a preferred aspect of the invention, the denture adhesive base composition may further include at least one cream base material selected from the group consisting of petrolatum, natural and synthetic oils and mixtures thereof.

In another preferred aspect of the invention, the denture adhesive base composition may further include a cream base material which is a combination of mineral oil with a minor amount of polyethylene wax having an average molecular weight of 1,000 to 20,000.

In another preferred aspect of the invention, the denture adhesive base composition may further include non-toxic, powdered, excipient materials.

The denture adhesive compositions and denture adhesive base compositions of this invention may be formulated to contain the methyl vinyl ethermaleic acid copolymer, polyvinyl pyrrolidone and ethylene oxide polymer in either powder or paste form. In the powder form, the components are admixed with the flavoring agents and colorants, together with other non-essential ingredients such as non-toxic anti-caking agents (silica, magnesium stearate, talcum powder or the like). The mixture of ingredients is thoroughly agitated or stirred to yield a generally homogenous intermixing of all components. In the paste formulations, the methyl vinyl ethermaleic acid copolymer, polyvinyl pyrrolidone and ethylene oxide polymers are admixed with petrolatum, along with the previously described waxes, oils, preservatives, flavoring agents, colorants, sweetening agents, viscosity modifiers and so forth.

A particularly preferred paste or cream formulation is prepared by utilizing as the cream or paste base, the product of U.S. Pat. No. 3,215,599, the disclosure of which is incorporated herein by reference. The cream or paste base of this patent is characterized as a mixture of white petroleum oil with a minor amount of a polyethylene wax having an average molecular weight of 1,000 to 20,000. This product is described as having emollient properties, useful in the formulation of medicaments where absorption of the medicaments by the skin is of paramount importance. Denture adhesive creams formulated with this petroleum oil/polyethylene wax blend as the paste or cream base display unusually good stability, extrudability and product appearance.

The method for preparing the denture adhesive compositions according to the present invention, whether formulated as a powder or paste, employs conventional types of mixing equipment which are known in the art for blending, heating and cooling solids and liquids.

The method for preparing the denture adhesive base compositions and denture adhesive composition containing the same may be conveniently prepared by mixing the components until a homogeneous mixture is obtained and recovering the resulting product. Preferably the base composition is prepared as a preblended formulation which can be mixed with the remaining components used to prepare the final formulation. Mixing is conveniently performed at temperatures suitable to melt the components to be blended. For example, if polyethylene and mineral oil are to be employed such material may be heated to temperatures from about 50° to 110° C., and are preferably cooled prior to blending with the base preblend. Flavoring agents may be added to the preblend and/or the wax/oil mixture prior to mixing in the final mixture.

Whether formulated as a powder or paste, the denture adhesive compositions and base compositions of this invention, when applied to dentures and exposed to moisture, hydrate to form adhesive compositions which exhibit unexpectedly superior characteristics in comparison with denture adhesives of the prior art. Once formulated the compositions may be used or stored for future use.

The following examples are given to illustrate the invention, but are not deemed to be limiting thereof. All percentages given throughout the specification are based on the weight of the final denture adhesive composition unless otherwise indicated.

EXAMPLE 1

Preparation of a Denture Adhesive Cream

A denture adhesive cream was prepared from the following ingredients:

| Ingredients | Percent w/w |
| --- | --- |
| Polyethylene | 5.26 |
| Mineral oil | 47.34 |
| Methyl vinyl ethermaleic acid copolymer | 16.2 |
| Polyvinyl pyrrolidone | 16.2 |
| Ethylene oxide polymer | 14.736 |
| Peppermint oil | 0.10 |
| Methyl paraben | 0.05 |
| Propyl paraben | 0.10 |
| Color | 0.014 |

A. Weigh polyethylene and mineral oil into a pot, and mix to form a homogenous mixture while raising the temperature to 90°-95° C. Check to assure complete solution of the wax. With continued mixing, cool to at least 45° C.

B. Add peppermint oil, methyl paraben and propyl paraben to the mixture from Step A and continue mixing until a homogenous blend is obtained.

C. Preblend the methyl vinyl ethermaleic acid copolymer, polyvinyl pyrrolidone, ethylene oxide polymer and color; add to the above mixture with continued mixing. After about 5 minutes scrape down as needed. Reduce pressure to about 28-29 inches vacuum and mix for about 5-10 additional minutes. The product is removed and stored for use:

This formulation was subjected to panel testing using the formulations of this Example with multiple panelists. The panelists were requested to use the denture adhesive according to the following instructions:

1. Thoroughly brush away any remaining adhesive and dry dentures.
2. Apply three short strips of adhesive. Keep strips away from edges. Use only the amount necessary. A few trials should indicate the proper amount and best placement of strips for your individual needs.
3. Press dentures firmly in place and hold for 20 seconds while cream sets.

The panelists were then requested to rate the denture adhesive for the following:
 (a) number of applications per day,
 (b) firmness of hold (7=excellent to 1=totally unusable),
 (c) duration of hold (in hours),
 (d) confidence of hold (1=very certain dentures would not hold, to 5=very certain dentures would hold), and
 (e) usage intent (1=definitely would not use, to 5=definitely would use).

The results are set forth in Table I.

EXAMPLE 2

Preparation of a Denture Adhesive Cream

A denture adhesive cream was prepared from the following ingredients:

| Ingredient | Percent w/w |
| --- | --- |
| Polyethylene | 5.26 |
| Mineral oil | 47.34 |
| Methyl vinyl ethermaleic acid copolymer | 11.8 |
| Polyvinyl pyrrolidone | 11.8 |
| Hydroxypropylcellulose | 11.636 |
| Ethylene oxide polymer | 11.9 |
| Peppermint oil | 0.10 |
| Methyl paraben | 0.05 |
| Propyl paraben | 0.10 |
| Color | 0.014 |

A. Weigh polyethylene and mineral oil into a pot, and mix to form a homogenous mixture while raising the temperature to 90°–95° C. Check to assure complete solution of the wax. With continued mixing, cool to at least 45° C.

B. Add peppermint oil, methyl paraben and propyl paraben to the mixture from Step A and continue mixing again until a homogenous blend is obtained.

C. Preblend the methyl vinyl ethermaleic acid copolymer, polyvinyl pyrrolidone, hydroxypropylcellulose, ethylene oxide polymer and color; add to the above mixture with continued mixing. After about 5 minutes scrape down as needed. Reduce pressure to about 28-29 inches vacuum and for about 5-10 additional minutes. The product is removed and stored for use.

The formulation of this Example was subjected to panel testing, following the testing procedure of Example 1. The panelists were requested to rate the denture adhesive according to the same criteria as described in Example 1.

The results are set forth in Table 2.

The invention being thus described, it will be obvious that the same may be varied in many ways. Such variations are not to be regarded as a departure from the spirit and scope of the invention and all such modifications are intended to be included within the scope of the following claims.

What is claimed is:

1. A denture adhesive base composition comprising a substantially anhydrous mixture of methyl vinyl ethermaleic acid copolymer, polyvinyl pyrrolidone and ethylene oxide polymer wherein said methyl vinyl ethermaleic acid copolymer is present in amounts of from about 20 to about 40 percent by weight, based on the total weight of the denture adhesive base composition, said polyvinyl pyrrolidone is present in amounts of from about 20 to about 40 percent by weight, based on the total weight of the denture adhesive base composition, and said ethylene oxide polymer is present in amounts of from about 20 to about 40 percent by weight, based on the total weight of the denture adhesive base composition.

2. The denture adhesive base composition of claim 1, wherein said methyl vinyl ethermaleic acid copolymer is present in amounts of from about 30 to about 35 percent by weight, based on the total weight of the denture adhesive base composition, said polyvinyl pyrrolidone is present in amounts of from about 30 to about 35 percent by weight, based on the total weight of the denture adhesive base composition, and said ethylene oxide polymer is present in amounts of from about 30 to about 35 percent by weight, based on the total weight of the denture adhesive base composition.

3. A denture adhesive composition which comprises a substantially anhydrous mixture of from about 25 to about 50 percent by weight, based on the total weight of the denture adhesive composition, of a denture adhesive base composition containing approximately equal amounts of methyl vinyl ethermaleic acid copolymer, polyvinyl pyrrolidone and ethylene oxide polymer.

4. The denture adhesive composition of claim 3, further including up to about 20 percent by weight, based on the total weight of the denture adhesive composition, of hydroxypropylcellulose.

5. The denture adhesive composition of claim 3, further including up to about 15 percent by weight, based on the total weight of the denture adhesive composition, of hydroxypropylcellulose.

6. The denture adhesive composition of claim 3, further including from about 8 to about 20 percent by weight, based on the total weight of the denture adhesive composition, of hysroxypropylcellulose.

7. A denture adhesive composition comprising a substantially anhydrous mixture of:
   (a) from about 25 to about 50 percent by weight, based on the total weight of the denture adhesive composition, of a denture adhesive base composition containing approximately equal amounts of methyl vinyl ethermaleic acid copolymer, polyvinyl pyrrolidone and ethylene oxide polymer;
   (b) from about 8 to about 20 percent by weight, based on the total weight of the denture adhesive composition, of hydroxypropylcellulose; and
   (c) from about 30 to about 67 percent by weight, based on the total weight of the denture adhesive composition, of additional materials selected from the group consisting of waxes, oils, preservatives, flavoring agents, colorants, sweetening agents, viscosity modifiers and mixtures thereof.

8. A denture adhesive composition comprising a substantially anhydrous mixture of:
   (a) from about 5 to about 20 percent by weight, based on the total weight of the denture adhesive composition, of methyl vinyl ethermaleic acid copolymer;
   (b) from about 5 to about 20 percent by weight, based on the total weight of the denture adhesive composition, of polyvinyl pyrrolidone;
   (c) from about 5 to about 20 percent by weight, based on the total weight of the denture adhesive composition, of ethylene oxide polymer;
   (d) from about 8 to about 20 percent by weight, based on the total weight of the denture adhesive composition, of hydroxypropylcellulose; and
   (e) additional materials in an amount sufficient to yield a denture adhesive composition having a total weight equal to 100 percent by weight of the total denture adhesive composition.

9. The denture adhesive composition of claim 8, wherein said additional materials are selected from the group consisting of waxes, oils, preservatives, flavoring agents, colorants, sweetening agents, viscosity modifiers and mixtures thereof.

10. The denture adhesive base composition of claim 1, further including at least one cream base material selected from the group consisting of petrolatum, natural and synthetic oils and mixtures thereof.

11. The denture adhesive base composition of claim 1, further including a cream base material which is a combination of mineral oil with a minor amount of a polyethylene wax having an average molecular weight of 1,000 to 20,000.

12. The denture adhesive base composition of claim 1, further including non-toxic, powdered, excipient materials.

13. The denture adhesive composition of claim 3, further including at least one cream base material selected from the group consisting of petrolatum, natural and synthetic oils and mixtures thereof.

14. The denture adhesive composition of claim 3, further including a cream base material which is a combination of mineral oil with a minor amount of a polyethylene wax having an average molecular weight of 1,000 to 20,000.

15. The denture adhesive composition of claim 3, further including non-toxic, powdered, excipient materials.

16. A method for preparing a denture adhesive base composition comprising:
  (a) preparing a substantially anhydrous mixture of from about 20 to about 40 percent by weight, based on the total weight of the denture adhesive base composition of methyl vinyl ethermaleic acid copolymer, from about 20 to about 40 percent by weight, based on the total weight of the denture adhesive base composition of polyvinyl pyrrolidone and from about 20 to about 40 percent by weight, based on the total weight of the denture adhesive base composition of ethylene oxide polymer;
  (b) forming a denture adhesive base composition including said mixture; and
  (c) recovering said denture adhesive base composition.

17. The method of claim 16, wherein said methyl vinyl ethermaleic acid copolymer is present in amounts of from about 30 to about 35 percent by weight, based on the total weight of the denture adhesive base composition, said polyvinyl pyrrolidone is present in amounts of from about 30 to about 35 percent by weight, based on the total weight of the denture adhesive base composition, and said ethylene oxide polymer is present in amounts of from about 30 to about 35 percent by weight, based on the total weight of the denture adhesive base composition.

18. A method for preparing a denture adhesive composition comprising:
  (a) preparing a substantially anhydrous mixture of from about 25 to about 50 percent by weight, based on the total weight of the denture adhesive composition, of a denture adhesive base composition containing approximately equal amounts of methyl vinyl ethermaleic acid copolymer, polyvinyl pyrrolidone and ethylene oxide polymer;
  (b) forming a denture adhesive composition including said denture adhesive base composition; and
  (c) recovering said denture adhesive composition.

19. The method of claim 18, wherein said denture adhesive composition further includes up to about 20 percent by weight, based on the total weight of the denture adhesive composition, of hydroxypropylcellulose.

20. The method of claim 18, wherein said denture adhesive composition further includes up to about 15 percent by weight, based on the total weight of the denture adhesive composition, of hydroxypropylcellulose.

21. The method of claim 18, wherein said denture adhesive composition further includes from about 8 to about 20 percent by weight, based on the total weight of the denture adhesive composition, of hydroxypropylcellulose.

22. A method for preparing a denture adhesive composition comprising:
  (a) preparing a substantially anhydrous mixture of:
    (i) from about 25 to about 50 percent by weight, based on the total weight of the denture adhesive composition, of a denture adhesive base composition containing approximately equal amounts of methyl vinyl ethermaleic acid copolymer, polyvinyl pyrrolidone and ethylene oxide polymer;
    (ii) from about 8 to about 20 percent by weight, based on the total weight of the denture adhesive composition, of hydroxypropylcellulose; and
    (iii) from about 30 to about 67 percent by weight, based on the total weight of the denture adhesive composition, of additional materials selected from the group consisting of waxes, oils, preservatives, flavoring agents, colorants, sweetening agents, viscosity modifiers and mixtures thereof.
  (b) forming a denture adhesive composition including said mixture; and
  (c) recovering said denture adhesive composition.

23. A method for preparing a denture adhesive composition comprising:
  (a) preparing a substantially anhydrous mixture of:
    (i) from about 5 to about 20 percent by weight, based on the total weight of the denture adhesive composition, of methyl vinyl ethermaleic acid copolymer;
    (ii) from about 5 to about 20 percent by weight, based on the total weight of the denture adhesive composition, of polyvinyl pyrrolidone;
    (iii) from about 5 to about 20 percent by weight, based on the total weight of the denture adhesive composition, of ethylene oxide polymer;
    (iv) from about 8 to about 20 percent by weight, based on the total weight of the denture adhesive composition, of hydroxypropylcellulose; and
    (v) additional materials in an amount sufficient to yield a denture adhesive composition having a total weight equal to 100 percent by weight of the total denture adhesive composition;
  (b) forming a denture adhesive composition including said mixture; and
  (c) recovering said denture adhesive composition.

24. The method of claim 23, wherein said additional materials are selected from the group consisting of waxes, oils, preservatives, flavoring agents, colorants, sweetening agents, viscosity modifiers and mixtures thereof.

25. The method of claim 16, wherein said denture adhesive base composition further includes at least one cream base material selected from the group consisting of petrolatum, natural and synthetic oils and mixtures thereof.

26. The method of claim 16, wherein said denture adhesive base composition further includes a cream base material which is a combination of mineral oil with a minor amount of a polyethylene wax having an average molecular weight of 1,000 to 20,000.

27. The method of claim 16, wherein said denture adhesive base composition further includes non-toxic, powdered, excipient materials.

28. The method of claim 18, wherein said denture adhesive composition further includes at least one cream base material selected from the group consisting of petrolatum, natural and synthetic oils and mixtures thereof.

29. The method of claim 18, wherein said denture adhesive composition further includes a cream base material which is a combination of mineral oil with a minor amount of a polyethylene wax having an average molecular weight of 1,000 to 20,000.

30. The method of claim 18, wherein said denture adhesive composition further includes non-toxic, powdered, excipient materials.

* * * * *